(12) United States Patent
Lee et al.

(10) Patent No.: US 6,376,632 B1
(45) Date of Patent: Apr. 23, 2002

(54) PHOTORESIST POLYMERS OF CARBOXYL-CONTAINING ALICYCLIC COMPOUNDS

(75) Inventors: Geun Su Lee; Jae Chang Jung; Min Ho Jung; Cheol Kyu Bok; Ki Ho Baik, all of Kyoungki-do (KR)

(73) Assignee: Hyundai Electronics Industries Co., Ltd., Kyoungki (KR)

( * ) Notice: Subject to any disclaimer, the term of this patent is extended or adjusted under 35 U.S.C. 154(b) by 0 days.

(21) Appl. No.: 09/850,177

(22) Filed: May 7, 2001

Related U.S. Application Data

(62) Division of application No. 09/302,064, filed on Apr. 29, 1999, now Pat. No. 6,265,130.

(30) Foreign Application Priority Data

Apr. 30, 1998 (KR) .............................. 98-16223

(51) Int. Cl.⁷ ..................... C08F 132/04; G03F 7/039
(52) U.S. Cl. ..................... 526/281; 526/283; 430/270.1
(58) Field of Search ............... 526/281, 283; 430/270.1

(56) References Cited

U.S. PATENT DOCUMENTS

| | | | |
|---|---|---|---|
| 3,370,047 A | 2/1968 | Raines ..................... | 260/78.5 |
| 4,011,386 A | 3/1977 | Matsumoto et al. | |
| 4,106,943 A | 8/1978 | Ikeda et al. | |
| 4,491,628 A | 1/1985 | Ito et al. ..................... | 430/176 |
| 4,883,740 A | 11/1989 | Schwalm et al. ........... | 430/270 |
| 5,087,677 A | 2/1992 | Brekner et al. ............. | 526/160 |
| 5,212,043 A | 5/1993 | Yamamoto et al. ......... | 430/192 |
| 5,252,427 A | 10/1993 | Bauer et al. ................ | 430/270 |
| 5,278,214 A | 1/1994 | Moriya et al. | |
| 5,585,219 A | 12/1996 | Kaimoto et al. ......... | 430/270.1 |
| 6,265,130 B1 * | 7/2001 | Lee et al. ..................... | 430/18 |

FOREIGN PATENT DOCUMENTS

| | | |
|---|---|---|
| DK | 128164 | 2/1977 |
| EP | 0071571 | 7/1982 |
| EP | 0789278 A2 | 2/1997 |
| EP | 794458 | 9/1997 |
| EP | 0836119 A1 | 11/1997 |
| GB | 0768813 | 2/1957 |
| GB | 1342112 | 5/1970 |
| GB | 1329997 | 9/1970 |
| GB | 2320717 | 6/1997 |
| GB | 2320501 A | 12/1997 |
| GB | 2320718 A | 12/1997 |
| GB | 2321060 | 1/1998 |
| JP | 05297591 | 4/1992 |
| JP | 10316720 | 2/1998 |
| WO | WO 96/37526 | 11/1996 |
| WO | WO 97/33198 | 9/1997 |
| WO | WO 99/14256 | 3/1999 |

OTHER PUBLICATIONS

Thomas I. Wallow, et al., "Evaluation of Cycloolefin–Maleic Anhydride Alternating Copolymers as Single–Layer Photoresist for 193nm Photolithography", 1996, Proc. SPIE, vol. 2724, 355–364.

R.D. Allen et al., "The Influence of Photoacid Structure on the Design and Performance of 193nm Resists", 1997, Journal of Photopolymer Science and Technology, vol. 10, 503–510.

(List continued on next page.)

*Primary Examiner*—John S. Chu
(74) *Attorney, Agent, or Firm*—Marshall, Gerstein & Borun.

(57) ABSTRACT

The present invention relates to a carboxyl-containing alicyclic compound represented by Chemical Formula 1:
[formula 1]
wherein, $R_1$ and $R_2$, which may be identical to or different from each other, represent hydrogen or a tert-butyl group; X represents hydrogen, hydroxy or oxygen; and n represents a number from 1 to 3. Compounds of the present invention are useful as monomers in a photoresist resin, and in a process for preparing the same.

2 Claims, 1 Drawing Sheet

OTHER PUBLICATIONS

Figure 1:

F.M. Houlihan et al., "A Commercially Viable 193nm single Layer Resist Platform", 1997 Journal of Photopolymer Science and Technology, vol. 10, 511–520.

J.C. Jung et al., "ArF Single Layer Resist Composed of Alicyclic Main Chain Containing Maleic Anhydride", 1997, Journal of Photopolymer Science and Technology, vol. 10, 529–533.

S. J. Choi et al., "New ArF Single–Layer Resist for 193–nm Lithography", 1997, Journal of Photopolymer Science and Technology, vol. 10, 521–528.

T. Hattori et al., "Synthesis and Dissolution Characteristics of Novel Alicyclic Polymer With Monoacid Ester Structures", 1997, Journal of Photopolymer Science and Technology, vol. 10, 535–544.

K. Nozaki and Ei Yaro, "New Protective Groups in Methacrylate Polymer for 193–nm Resists", 1997, Journal of Photopolymer Science and Technology, vol. 10, 545–550.

K. Nakano et al., "Chemically Amplified Resist Based on High Etch–Resistant Polymer for 193–nm Lithography", 1997, Journal of Photopolymer Science and Technology, vol. 10, 561–569.

Alexander A. Dobrev, Emile Perez, Jean Claud Ader, Armand Lattes, "First Application of Functionalized in the Ester Moiety Acrylates in Diels–Alder Reaction: Invluence of Solvents on Stereochemistry": Bulgarian Chemical Communications, vol. 28, No. 2 (1995) pp. 253–258.

T.P. McGovern and C.E. Schreck, "Mosquito Repellents: Monocarboxylic Esters of Aliphatic Diols", Journal of the American Mosquito Control Association, vol. 4, No. 3, pp. 314–321.

CA Register No. 100207–98–5.
CA Register No. 32759–57–2.
CA Register No. 27056–70–8.
CA Register No. 174659–58–6.
CA Register No. 28503–41–5.
CA Register No. 194997–59–6.
CA Abstract No. 104:149512 & Macromolecules 19(4) 1266-8 (1986).
CA Abstract No. 91:124064 & Makromol. Chem. 180(8) 1975–88 (1979).
CA Abstract No. 113:24734 & JP 02 051511.
CA Abstract No. 127:227269 & J Photopolym. Sci. Technol. 10(4) 529–534 (1997).
CA Abstract No. 124:317926 & Marcomol. Rapid Commun. 17(3) 173–180 (1996).
CA Abstract No. 124:203171 & Macromolecules 29(8) 2755–63 (1996).
CA Abstract No. 127:227308 & Proc. SPIE–Int. Soc. Opt. Eng. (1997) 3049 Advances in Resist Technology and Processing XIV 92–103.
CA Abstract No. 66:18889 & Magy, Kem. Foly, (1966) 72(11)491–3.
CA Abstract No. 199328–07–9.

* cited by examiner

PHOTORESIST POLYMERS OF CARBOXYL-CONTAINING ALICYCLIC COMPOUNDS

This is a divisional application of U.S. application Ser. No. 09/302,064, filed Apr. 29, 1999 now U.S. Pat. No. 6,265,130.

FIELD OF THE INVENTION

The present invention relates to a carboxyl-containing alicyclic compound as a useful monomer for preparing a photoresist resin and a process for preparing the same. More specifically, the present invention relates to a carboxyl-containing alicyclic compound which is useful as a monomer for synthesizing a photoresist resin for an E-beam (electron-beam), KrF, ArF, an X-ray or EUV which can be applied to a high-density micro-pattern of not more than 0.15 µm (DRAM of 1 G or more).

BACKGROUND OF THE INVENTION

Most of the conventional ArF photoresist resins have low-etching resistance and insufficient resolution. Physical properties of a photoresist resin are affected by the type of monomers used for preparing the resin, and the production cost of a photoresist resin is very high because of the high price of the monomers used for the resin, so that mass production of the photoresist resin has been restricted. Thus, a lot of attempts have been made to develop the most proper monomer for economically producing a photoresist resin having excellent resolution and etching resistance on a large scale.

SUMMARY OF THE INVENTION

The object of the present invention is to provide photoresist monomers and copolymers which are appropriate for a lithography process using a light source having a short wavelength of not more than 250 nm.

The present invention also provides photoresist compositions comprising said copolymers.

Furthermore, the present invention provides a process for forming a photoresist pattern by using said photoresist composition and a process for preparing a semiconductor element therefrom.

DETAILED DESCRIPTION OF THE INVENTION

Now, the present Invention is described in more detail.

The present inventors have discovered the surprising fact that the alicyclic compounds represented by Chemical Formula 1 below, which have one or more carboxylic groups or tert-butyl groups, are useful as a monomer employed in the synthesis of a photoresist resin for an ArF, EUV, E-beam or X-ray light source. The compounds of the present invention have high purity and low price, so that a photoresist resin of high performance can be economically produced on a large scale therefrom.

[Chemical Formula 1]

In the above formula, $R_1$ and $R_2$, which may be identical to or different from each other, represent hydrogen or a tert-butyl group; X represents hydrogen, hydroxy or oxygen; and n represents a number from 1 to 3.

Furthermore, the present inventors have found that an excellent pattern can be obtained in a lithography process employing a light source of an extremely short wavelength, by using a photoresist composition comprising the compound represented by Chemical Formula 1.

Among the carboxyl-containing alicyclic compounds of the present invention represented by Chemical Formula 1, preferred compounds are listed below:

(a) Compounds of the following formula wherein $R_1$ and R2 individually represent tert-butyl and X represents oxygen, such as 5-norbornene-2-carbonyl di-tert-butyl malonate; bicyclo[2,2,2]oct-5-ene-2-carbonyl di-tert-butyl malonate; or bicyclo[3,2,2]non-8-ene-2-carbonyl di-tert-butyl malonate:

[Formula 1a]

(b) Compounds of the following formula wherein R1 is tert-butyl, $R_2$ is hydrogen and X is oxygen, such as 5-norbornene-2-carbonyl mono-tert-butyl malonate; bicyclo[2,2,2]oct-5-ene-2-carbonyl mono-tert-butyl malonate; or bicyclo[3,2,2]non-8-ene-2-carbonyl mono-tert-butyl malonate:

[Formula 1b]

(c) Compounds of the following formula wherein $R_1$ and $R_2$ individually represent hydrogen and X represents oxygen, such as 5-norbornene-2-carbonyl malonic acid; bicyclo[2,2,2]oct-5-ene-2-carbonyl malonic acid; or bicyclo[3,2,2]non-8-ene-2-carbonyl malonic acid:

[Formula 1c]

(d) Compounds of the following formula wherein $R_1$ and $R_2$ individually represent tert-butyl and X represents the hydroxy group, such as 5-norbornene-2-yl di-tert-butylhydroxymethyl malonate; bicyclo[2,2,2]oct-5-ene-2-yl di-tert-butylhydroxymethyl malonate; or bicyclo[3,2,2]non-8-ene-2-yl di-tert-butylhydroxymethyl malonate:

[Formula 1d]

(e) Compounds of the following formula wherein $R_1$ is tert-butyl, $R_2$ is hydrogen and X is a hydroxy group, such as 5-norbornene-2-yl mono-tert-butylhydroxymethyl malonate; bicyclo[2,2,2]oct-5-ene-2-yl mono-tert-butylhydroxymethyl malonate; or bicyclo[3,2,2]non-8-ene-2-yl mono-tert-butylhydroxymethyl malonate:

[Formula 1e]

(f) Compounds of the following formula wherein $R_1$ and $R_2$ individually represent hydrogen and X represents a hydroxy group, such as 5-norbornene-2-yl hydroxymethylmalonic acid; bicyclo[2,2,2]oct-5-ene-2-yl hydroxymethylmalonic acid; or bicyclo[3,2,2]non-8-ene-2-yl hydroxymethylmalonic acid:

[Formula 1f]

(g) Compounds of the following formula wherein $R_1$ and $R_2$ individually represent tert-butyl and X represents hydrogen, such as 5-norbornene-2-yl di-tert-butylmethyl malonate; bicyclo[2,2,2]oct-5-ene-2-yl di-tert-butylmethyl malonate; or bicyclo[3,2,2]non-8-ene-2-yl di-tert-butylmethyl malonate:

[Formula 1g]

(h) Compounds of the following formula wherein $R_1$ is tert-butyl, $R_2$ is hydrogen and X is hydrogen, such as 5-norbornene-2-yl mono-tert-butylmethyl malonate; bicyclo[2,2,2]oct-5-ene-2-yl mono-tert-butylmethyl malonate; or bicyclo[3,2,2]non-8-ene-2-yl mono-tert-butylmethyl malonate:

[Formula 1h]

(i) Compounds of the following formula wherein $R_1$, $R_2$ and X individually represent hydrogen, such as 5-norbornene-2-yl methylmalonic acid; bicyclo[2,2,2]oct-5-ene-2-yl methylmalonic acid; or bicyclo[3,2,2]non-8-ene-2-yl methyl malonic acid.

[Formula 1i]

The carboxyl-containing alicyclic compound of the present invention, represented by Chemical Formula 1, can be prepared by reacting a compound represented by Chemical Formula 2 below with a malonate represented by Chemical Formula 3:

in the presence of a solvent such as tetrahydrofuran (THF), dimethylformamide (DMF) or dioxane.

[Chemical Formula 2]

In Formula 2 above, $R_3$ represents hydrogen, or halogen such as chloro, bromo and iodo, Y represents hydrogen or oxygen, n is a number from 1 to 3, and $R_4$ and $R_5$, which may be identical to or different from each other, represent the tert-butyl group or a sodium ion.

The compound represented by Chemical Formula 2, which is used as a starting material in the present invention can be prepared as follows:

The alicyclic compound of Chemical Formula 2 wherein $R_3$ is hydrogen or halogen and Y is oxygen, is prepared by reacting 1,3-cyclopentadiene, 1,3-cyclohexadiene or 1,3-cycloheptadiene with acroyl halide or acrolein at a temperature between −40° C. to 80° C., preferably between −20° C. to 30° C. in an equivalent ratio of 1:1, as shown in the following Reaction Scheme A:

[Reaction Scheme A]

The alicyclic compound of Chemical Formula 2 wherein $R_3$ is a halogen such as bromo, chloro or iodo and Y is hydrogen, is prepared by reacting 5-norbornene-2-methanol, [2,2,2]bicyclooctene-2-methanol or [3,2,2]bicyclononene-6-methanol with some excess of thionyl chloride (1.2 equiv.) at a temperature between −40° C. to 80° C., preferably between 0° C. to 25° C., as shown in the following reaction scheme B:

[Reaction Scheme B]

The malonic acid compounds of the present invention, represented by Chemical Formula 3, include:

sodium salt of di-tert-butyl malonate;

sodium salt of mono-tert-butyl malonate;

sodium malonate;

In the process according to the present invention, the compound of Chemical Formula 2 and malonate salt of Chemical Formula 3 are preferably reacted in a molar ratio of 1:1. As a reaction solvent, tetrahydrofuran (THF), dimethylformamide (DMF), dioxane, or the like is used, and the amount of the solvent is preferably in a 5 to 50 weight ratio to the compound of Chemical Formula 2.

Synthesis of a Photoresist Copolymer

A photoresist polymer according to the present invention can be obtained by copolymerizing a photoresist monomer of the present invention with one or more compound(s) represented by Chemical Formula 4:

[Chemical Formula 4]

wherein, i represents a number from 1 to 3, m and n independently represent a number from 1 to 3, and $R_6$ and $R_7$ independently represent an alkyl group or a cyclic alkyl group having 0 to 10 carbon atoms.

The copolymer resin (Chemical Formulas 4–7) of the present invention can be prepared according to conventional techniques such as bulk polymerization, solution polymerization, or the like. Polymerization initiators which can be used in the present invention include benzoyl peroxide, 2,2'-azobisisobutyronitrile (AIBN), acetyl peroxide, lauryl peroxide, tert-butyl peracetate, di-tert-butyl peroxide, and the like. As a solvent, cyclohexanone, methyl ethyl ketone, benzene, toluene, dioxane, dimethylformamide may be used individually or as a mixed solvent.

As to the polymerization conditions used in preparing the copolymer resin according to the present invention, conventional radical polymerization temperatures and pressures may be adjusted depending on the properties of the reactants, but polymerization is preferably carried out at a temperature between 60° C.–200° C. In a nitrogen or an argon atmosphere for 4–24 hours.

Preferable photoresist copolymers according to the present invention include the compound represented by the following Chemical Formula 5:

[Chemical Formula 5]

wherein, i and k independently represent numbers from 1 to 3, c is 1 or 2, m and n independently represent a number from 1 to 3, $R_6$ and $R_7$ independently represent an alkyl group or a cyclic alkyl croup having 0 to 10 carbon atoms, and a, b, c and d individually represent polymerization ratios of each comonomer, preferably, a=5–20 mol %, b=50 mol %, c=0–30 mol % and d=5–20 mol %.

As a solvent for purifying the copolymer by crystallization, alcohols (methanol, ethanol, isopropanol) or petroleum ether may be used instead of diethyl ether.

[Chemical Formula 6]

Preparation of Photoresist Composition and Pattern Formation

The copolymer resin according to the present invention can be used in forming a positive micro-image by mixing a conventional inorganic photoacid generator in an organic solvent according to a conventional process for preparing a photoresist solution. In the process of forming a photosensitive film pattern on a semiconductor element, the amount of the copolymer resin of the present invention can be varied depending upon the type of organic solvent or inorganic photoacid generator used, or the lithography conditions. However, about 10–30 wt % of the copolymer based on the organic solvent used in preparing the photoresist is generally used.

Now, the process for forming a photosensitive film pattern of a semiconductor element by using the copolymer of the present invention is described in more detail.

A copolymer of the present invention is dissolved in cyclohexanone to provide a concentration of 10–13% by weight, and an onium salt or organic sulfonic acid as an inorganic photoacid generator is incorporated thereto in a concentration of 0.1–10% by weight, and the solution is filtered with an ultra-micro filter to prepare a photoresist solution. Usable inorganic photoacid generators include triphenylsulfonium triplate, dibutylnaphthylsulfonium triplate, 2,6-dimethylphenylsulfonate, bis(arylsulfonyl)-diazomethane, oxime sulfonate and 2,1-diazonaphthoquinon-4-sulfonate.

As an organic solvent, ethyl 3-ethoxypropionate, methyl 3-methoxypropionate, propyleneglycol methyl ether acetate, or the like may be used instead of cyclohexanone. The amount of the solvent is preferably 200 to 1000% by weight based on the amount of the photoresist resin used.

The photoresist solution thus prepared is spin-coated on a silicon wafer to prepare a thin film, and the wafer is preheated in an oven or a hot plate at 80°–150° C. for 1–5 minutes, exposed to light by using a far ultraviolet light exposer device or excimer laser exposer device, and then post-heated at a temperature between 100°–200° C. for 1 second to 5 minutes. The resulting, exposed wafer is impregnated in 2.38% aqueous TMAH solution for 1–1.5 minutes to obtain a positive resist pattern.

ArF, KrF, an E-beam, EUV (extreme ultraviolet) or an ion beam may also be used as a light exposer. The energy of the light exposure is preferably 0.1–10 Mj/cm$^2$.

DETAILED DESCRIPTION OF PREFERRED EMBODIMENT

Now, the present invention is described in more detail by referring to the Examples. However, it should not be understood that the technical scope of the present invention is restricted to these Examples by any means.

PREPARATION EXAMPLE 1

Synthesis of 5-norbornene-2-carbonyl chloride 1,3-Cyclopentadiene (1 equiv.) is reacted with acroyl chloride (1 equiv.) at −20° C. for 1 hour, and the temperature of the reaction mixture is slowly raised to room temperature (23° C.), and the mixture is reacted at the same temperature for 12 hours. When the reaction is completed, the solvent is removed by evaporation, and the resultant compound is distilled in vacuo to obtain the pure title compound (118 g) as a colorless and transparent liquid (purity: 99%, yield: 97%).

PREPARATION EXAMPLE 2

Synthesis of bicyclo[2,2,2]oct-5-ene-2-carbonyl chloride

The same procedure of Preparation Example 1 is repeated but 1,3-cyclohexadiene (1 equiv.) is used instead of 1,3-cyclopentadiene, to obtain the pure title compound (153 g) as a colorless and transparent liquid (purity: 99%, yield: 98%).

PREPARATION EXAMPLE 3

Synthesis of bicyclo[3,2,2]non-8-ene-2-carbonyl chloride

The same procedure of Preparation Example 1 is repeated but 1,3-cycloheptadiene (1 equiv.) is used instead of 1,3-cyclopentadiene, to obtain the pure title compound (171 g) as a colorless and transparent liquid (purity: 99%, yield: 95%).

PREPARATION EXAMPLE 4

Synthesis of 5-norbornene-2-carboaldehyde

The same procedure of Preparation Example 1 is repeated but acrolein (1 equiv.) is used instead of acroyl chloride, to obtain the pure title compound (131 g) as a colorless and transparent liquid (purity: 99%, yield: 98%).

PREPARATION EXAMPLE 5

Synthesis of bicyclo[2,2,2]-oct-5-ene-2-carboaldehyde

The same procedure of Preparation Example 2 is repeated but acrolein (1 equiv.) is used instead of acroyl chloride, to obtain the pure title compound (129 g) as a colorless and transparent liquid (purity: 99%, yield: 96%).

PREPARATION EXAMPLE 6

Synthesis of bicyclo[3,2,2]-non-8-ene-2-carboaldehyde

The same procedure of Preparation Example 3 is repeated but acrolein (1 equiv.) is used instead of acroyl chloride, to obtain the pure title compound (142 g) as a colorless and transparent liquid (purity: 99%, yield: 97%).

PREPARATION EXAMPLE 7

Synthesis of 5-norbornene-2-methyl chloride

To a solution of 5-norbornene-2-methanol (1 equiv.) in dichloromethane solvent (300 g), some excess of thionyl chloride (1.2 equiv.) is slowly added, and the mixture is reacted at 15° C. for 24 hours. After the reaction is completed, excess thionyl chloride is removed by washing with 10% aqueous sodium carbonate solution, and the reaction mixture is extracted by adding ethyl acetate (700 g) and water (1 liter). The ethyl acetate layer is dried over anhydrous magnesium sulfate, filtered and evaporated. After distilling the resultant product under reduced pressure, the pure title compound (134 g) is obtained as a colorless and transparent liquid (purity: 99%, yield: 94%).

PREPARATION EXAMPLE 8

Synthesis of bicyclo[2,2,2]oct-5-ene-2-methyl chloride

To a solution of [2,2,2]bicyclooctene-2-methanol (1 equiv.) in dichloromethane solvent (300 g), some excess of thionyl chloride (1.2 equiv.) is slowly added at 10° C., and the reaction mixture is treated according to the same procedure as Preparation Example 7, to give 147 g of the pure title compound (purity: 99%, yield: 95%).

PREPARATION EXAMPLE 9

Synthesis of bicyclo[3,2,2]non-8-ene-2-methyl chloride

The same procedure of Preparation Example 8 is repeated but [3,2,2]bicyclononene-6-methanol (1 equiv.) is used instead of [2,2,2]bicyclooctene-2-methanol, to obtain 157 g of the pure title compound (purity: 99%, yield: 94%).

EXAMPLE 1

Synthesis of 5-norbornene-2-carbonyl di-tert-butyl malonate

First, di-tert-butyl malonate (22 g) is reacted with NaOH (2.5 g) in dry tetrahydrofuran (200 g) to prepare the sodium salt of di-tert-butyl malonate. To the resultant solution, 5-norbornene-2-carbonyl chloride (15.7 g) obtained in Preparation Example 1 is slowly added, and the mixture is reacted at −20° C. in a nitrogen atmosphere for 1 hour, and further reacted at 40° C. for 7 hours. After the reaction is completed, the solvent is distilled off, and the residue is acidified with a diluted 1N sulfuric acid or a hydrochloric acid solution, and extracted with ethyl acetate. The organic layer is dried over anhydrous magnesium sulfate and filtered. The resultant organic layer is distilled and recrystallized to obtain 26 g of the pure title compound (purity: 99%, yield: 80%).

EXAMPLE 2

Synthesis of bicyclo[2,2,2]oct-5-ene-2-carbonyl di-tert-butyl malonate

To a solution of sodium salt of di-tert-butyl malonate (24 g) prepared according to the same procedure as in Example 1 in dry tetrahydrofuran (200 g), bicyclo[2,2,2]oct-5-ene-2-carbonyl chloride (17.1 g) obtained in Preparation Example 2 is slowly added, and the reaction mixture is reacted at −20° C. in a nitrogen atmosphere for 1 hour, and further reacted at 40° C. for 10 hours. Then, the mixture is worked up as in the procedure of Example 1, to obtain 28 g of the pure title compound (purity: 98%, yield: 82%).

EXAMPLE 3

Synthesis of bicyclo[3,2,2]non-8-ene-2-carbonyl di-tert-butyl malonate

To a solution of sodium salt of di-tert-butyl malonate (24 g) prepared according to the same procedure as in Example 1 in dry tetrahydrofuran (200 g), bicyclo[3,2,2]non-8-ene-2-carbonyl chloride (18.4 g) obtained in Preparation Example 3 is slowly added, and the reaction mixture is reacted at −20° C. in a nitrogen atmosphere for 1 hour, and further reacted at 40° C. for 8 hours. Then, the mixture is worked up as in the procedure of Example 1, to obtain 28 g of the pure title compound (purity: 98%, yield: 77%).

EXAMPLE 4

Synthesis of 5-norbornene-2-carbonyl di-tert-butyl malonate

First, mono-tert-butyl malonate (16 g) is reacted with NaOH (4.8 g) in dry tetrahydrofuran (200 g) to prepare the sodium salt of mono-tert-butyl malonate. To the resultant solution, 5-norbornene-2-carbonyl chloride (15.7 g) obtained in Preparation Example 1 is slowly added, and the mixture is reacted at −20° C. in a nitrogen atmosphere for 1 hour, and further reacted at 40° C. for 9 hours. Then, the mixture is worked up as in the procedure of Example 1, to obtain 24 g of the pure title compound (purity: 99%, yield: 86%).

EXAMPLE 5

Synthesis of bicyclo[2,2,2]oct-5-ene-2-carbonyl mono-tert-butyl malonate

To a solution of sodium salt of mono-tert-butyl malonate (20.4 g) prepared according to the same procedure as in Example 4, bicyclo[2,2,2]oct-5-ene-2-carbonyl chloride (17.1 g) obtained in Preparation Example 2 is slowly added, and the reaction mixture is reacted at −20° C. in a nitrogen atmosphere for 1 hour, and further reacted at 40° C. for 6 hours. Then, the mixture is worked up as in the procedure of Example 1, to obtain 25 g of the pure title compound (purity: 99%, yield: 84%).

EXAMPLE 6

Synthesis of bicyclo[3,2,2]non-8-ene-2-carbonyl mono-tert-butyl malonate

To a solution of sodium salt of mono-tert-butyl malonate (20.4 g) prepared according to the same procedure as in Example 4, bicyclo[3,2,2]non-8-ene-2-carbonyl chloride (18.5 g) obtained in Preparation Example 3 is slowly added, and the reaction mixture is reacted at −20° C. in a nitrogen atmosphere for 1 hour, and further reacted at 55° C. for 8 hours. Then, the mixture is worked up as in the procedure of Example 1, to obtain 25 g of the pure title compound (purity: 99%, yield: 82%).

EXAMPLE 7

Synthesis of 5-norbornene-2-carbonyl malonic acid

First, malonic acid (10.4 g) is reacted with NaOH (7.5 g) in dry tetrahydrofuran (200 g) to prepare sodium malonate. To the resultant solution, 5-norbornene-2-carbonyl chloride (15.7 g) obtained in Preparation Example 1 is slowly added, and the mixture is reacted at −20° C. in a nitrogen atmosphere for 1 hour, and further reacted at 45° C. for 10 hours. Then, the mixture is worked up as in the procedure of Example 1, to obtain 20 g of the pure title compound (purity: 98%, yield: 89%).

EXAMPLE 8

Synthesis of bicyclo[2,2,2]oct-5-ene-2-carbonyl malonic acid

To a solution containing sodium malonate (17.1 g) which was prepared according to the same procedure as in Example 7, bicyclo[2,2,2]oct-5-ene-2-carbonyl chloride (17.1 g) obtained in Preparation Example 2 is slowly added, and the reaction mixture is reacted at −20° C. in a nitrogen atmosphere for 1 hour, and further reacted at 60° C. for 9 hours. Then, the mixture is worked up as in the procedure of Example 1, to obtain 21 g of the pure title compound (purity: 99%, yield: 88%).

EXAMPLE 9

Synthesis of bicyclo[3,2,2]non-8-ene-2-carbonyl malonic acid

To a solution containing sodium malonate (17.1 g) which was prepared according to the same procedure as in Example 7, bicyclo[3,2,2]non-8-ene-2-carbonyl chloride (18.4 g) obtained in Preparation Example 3 is slowly added, and the reaction mixture is reacted at −20° C. in a nitrogen atmosphere for 1 hour, and further reacted at 45° C. for 8 hours. Then, the mixture is worked up as in the procedure of Example 1, to obtain 22 g of the pure title compound (purity: 99%, yield: 87%).

EXAMPLE 10

Synthesis of 5-norbornene-2-yl di-tert-butylhydroxymethylmalonate

To a solution containing sodium salt of di-tert-butyl malonate (24 g) which was prepared according to the same procedure as in Example 1 in dry tetrahydrofuran (100 g), 5-norbornene-2-carboxaldehyde (12.2 g) obtained in Preparation Example 4 is added, and the reaction is carried out at −20° C. in a nitrogen atmosphere for 1 hour, and then at 60° C. for 10 hours. Then, the mixture is worked up as in the procedure of Example 1, to obtain 31 g of the pure title compound (purity: 98%, yield: 91%).

EXAMPLE 11

Synthesis of bicyclo[2,2,2]oct-5-ene-2-yl di-tert-butylhydroxymethylmalonate

To a solution containing sodium salt of di-tert-butyl malonate (24 g) which was prepared according to the same

EXAMPLE 12

Synthesis of bicyclo[3,2,2]non-8-ene-2-yl di-tert-butylhydroxymethylmalonate

To a solution containing sodium salt of di-tert-butyl malonate (24 g) which was prepared according to the same procedure as in Example 1 in dry tetrahydrofuran (100 g), bicyclo[3,2,2]non-8-ene-2-carboxaldehyde (15 g) obtained in Preparation Example 6 is slowly added, and the reaction is carried out at −20° C. in a nitrogen atmosphere for 1 hour, and then at 50° C. for 10 hours. Then, the reaction mixture is worked up as in the procedure of Example 1, to obtain 32 g of the pure title compound (purity: 98%, yield: 88%).

EXAMPLE 13

Synthesis of 5-norbornene-2-yl mono-tert-butylhydroxymethylmalonate

To a solution containing sodium salt of mono-tert-butyl malonate (20.4 g) which was prepared according to the same procedure as in Example 4 in dry tetrahydrofuran (100 g), 5-norbornene-2-carboxaldehyde (12.2 g) obtained in Preparation Example 4 is slowly added, and the reaction is carried out at −20° C. in a nitrogen atmosphere for 1 hour, and then at 50° C. for 10 hours. Then, the mixture is worked up as in the procedure of Example 1, to obtain 26 g of the pure title compound (purity: 99%, yield: 91%).

EXAMPLE 14

Synthesis of bicyclo[2,2,2]oct-5-ene-2-yl mono-tert-butylhydroxymethylmalonate

To a solution containing sodium salt of mono-tert-butyl malonate (20.4 g) which was prepared according to the same procedure as in Example 4 in dry tetrahydrofuran (100 g), bicyclo[2,2,2]oct-5-ene-2-carboxaldehyde (13.6 g) obtained in Preparation Example 5 is slowly added, and the reaction is carried out at −20° C. in a nitrogen atmosphere for 1 hour, and then at 50° C. for 10 hours. Then, the reaction mixture is worked up as in the procedure of Example 1, to obtain 26 g of the pure title compound (purity: 98%, yield: 89%).

EXAMPLE 15

Synthesis of bicyclo[3,2,2]non-8-ene-2-yl mono-tert-butylhydroxymethylmalonate

To a solution containing sodium salt of mono-tert-butyl malonate (20.4 g) which was prepared according to the same procedure as in Example 4 in dry tetrahydrofuran (100 g), bicyclo[3,2,2]non-8-ene-2-carboxaldehyde (15.0 g) obtained in Preparation Example 6 is slowly added, and the reaction is carried out at −20° C. in a nitrogen atmosphere for 1 hour, and then at 50° C. for 10 hours. Then, the reaction mixture is worked up as in the procedure of Example 1, to obtain 26 g of the pure title compound (purity: 99%, yield: 85%).

EXAMPLE 16

Synthesis of 5-norbornene-2-yl hydroxymethylmalonic acid

To a solution containing sodium malonate (17.0 g) of Example 7 in dry tetrahydrofuran (100 g), 5-norbornene-2-carboxaldehyde (12.2 g) obtained in Preparation Example 4 is slowly added, and the reaction is carried out at −20° C. in a nitrogen atmosphere for 1 hour, and then at 60° C. for 9 hours. Then, the mixture is worked up as in the procedure of Example 1, to obtain 21 g of the pure title compound (purity: 99%, yield: 93%).

EXAMPLE 17

Synthesis of bicyclo[2,2,2]oct-5-ene-2-yl hydroxymethylmalonic acid

To a solution containing sodium malonate (17.0 g) of Example 7 in dry tetrahydrofuran (100 g), bicyclo[2,2,2]oct-5-ene-2-carboxaldehyde (13.6 g) obtained in Preparation Example 5 is slowly added, and the reaction is carried out at −20° C. in a nitrogen atmosphere for 1 hour, and then at 50° C. for 10 hours. Then, the reaction mixture is worked up as in the procedure of Example 1, to obtain 22 g of the pure title compound (purity: 99%, yield: 92%).

EXAMPLE 18

Synthesis of bicyclo[3,2,2]non-8-ene-2-ylhydroxymethylmalonic acid

To a solution containing sodium malonate (17.0 g) of Example 7 in dry tetrahydrofuran (100 g), bicyclo[3,2,2]non-8-ene-2-carboxaldehyde (15 g) obtained in Preparation Example 6 is slowly added, and the reaction is carried out at −20° C. in a nitrogen atmosphere for 1 hour, and then at 50° C. for 10 hours. Then, the reaction mixture is worked up as in the procedure of Example 1, to obtain 24 g of the pure title compound (purity: 99%, yield: 90%).

EXAMPLE 19

Synthesis of 5-norbornene-2-yl di-tert-butylmethylmalonate

To a solution containing sodium malonate (17.0 g) of Example 7 in dry tetrahydrofuran (100 g), 5-norbornene-2-methyl chloride (14.3 g) obtained in Preparation Example 7 is slowly added, and the reaction is carried out at −20° C. in a nitrogen atmosphere for 1 hour, and then at 50° C. for 20 hours. Then, the mixture is worked up as in the procedure of Example 1, to obtain 24 g of the pure title compound (purity: 99%, yield: 87%).

EXAMPLE 20

Synthesis of bicyclo[2,2,2]oct-5-ene-2-yl di-tert-butylmethylmalonate

To a solution containing sodium salt of di-tert-butyl malonate (24.0 g) of Example 1 in dry tetrahydrofuran (100 g), bicyclo[2,2,2]oct-5-ene-2-methyl chloride (15.7 g) obtained in Preparation Example 8 is slowly added, and the reaction is carried out at −20° C. in a nitrogen atmosphere for 1 hour, and then at 60° C. for 24 hours. Then, the reaction mixture is worked up as in the procedure of Example 1, to obtain 29 g of the pure title compound (purity: 99%, yield: 86%).

EXAMPLE 21

Synthesis of bicyclo[3,2,2]non-8-ene-2-yl di-tert-butylmethylmalonate

To a solution containing sodium salt of di-tert-butyl malonate (24.0 g) of Example 1 in dry tetrahydrofuran (100 g), bicyclo[3,2,2]non-8-ene-2-methyl chloride (17.1 g) obtained in Preparation Example 9 is slowly added, and the reaction is carried out at −20° C. in a nitrogen atmosphere for 1 hour, and then at 50° C. for 24 hours. Then, the reaction mixture is worked up as in the procedure of Example 1, to obtain 29 g of the pure title compound (purity: 99%, yield: 88%).

EXAMPLE 22

Synthesis of 5-norbornene-2-yl mono-tert-butylmethylmalonate

To a solution containing sodium salt of mono-tert-butyl malonate (20.4 g) of Example 4 in dry tetrahydrofuran (100 g), 5-norbornene-2-methyl chloride (14.3 g) obtained in Preparation Example 7 is slowly added, and the reaction is carried out at −20° C. in a nitrogen atmosphere for 1 hour, and then at 55° C. for 24 hours. Then, the mixture is worked up as in the procedure of Example 1, to obtain 24 g of the pure title compound (purity: 99%, yield: 91%).

EXAMPLE 23

Synthesis of bicyclo[2,2,2]oct-5-ene-2-yl mono-tert-butylmethylmalonate

To a solution containing sodium salt of mono-tert-butyl malonate (20.4 g) of Example 4 in dry tetrahydrofuran (100 g), bicyclo[2,2,2]oct-5-ene-2-methyl chloride (15.7 g) obtained in Preparation Example 8 is slowly added, and the reaction is carried out at −20° C. in a nitrogen atmosphere for 1 hour, and then at 60° C. for 24 hours. Then, the reaction mixture is worked up as in the procedure of Example 1, to obtain 25 g of the pure title compound (purity: 99%, yield: 90%).

EXAMPLE 24

Synthesis of bicyclo[3,2,2]non-8-ene-2-yl mono-tert-butylmethylmalonate

To a solution containing sodium salt of mono-tert-butyl malonate (20.4 g) of Example 4 in dry tetrahydrofuran (100 g), bicyclo[3,2,2]non-8-ene-2-methyl chloride (17.1 g) obtained in Preparation Example 9 is slowly added, and the reaction is carried out at −20° C. in a nitrogen atmosphere for 1 hour, and then at 50° C. for 24 hours. Then, the reaction mixture is worked up as in the procedure of Example 1, to obtain 27 g of the pure title compound (purity: 99%, yield: 93%).

EXAMPLE 25

Synthesis of 5-norbornene-2-yl methylmalonic acid

To a solution containing sodium malonate (17 g) of Example 7 in dry tetrahydrofuran (100 g), 5-norbornene-2-methyl chloride (14.3 g) obtained in Preparation Example 7 is slowly added, and the reaction is carried out at −20° C. in a nitrogen atmosphere for 1 hour, and then at 50° C. for 24 hours. Then, the mixture is worked up as in the procedure of Example 1, to obtain 20 g of the pure title compound (purity: 99%, yield: 95%).

EXAMPLE 26

Synthesis of bicyclo[2,2,2]oct-5-ene-2-yl methylmalonic acid

To a solution containing sodium malonate (17 g) of Example 7 in dry tetrahydrofuran (100 g), bicyclo[2,2,2] oct-5-ene-2-methyl chloride (15.7 g) obtained in Preparation Example 8 is slowly added, and the reaction is carried out at −20° C. in a nitrogen atmosphere for 1 hour, and then at 50° C. for 24 hours. Then, the reaction mixture is worked up as in the procedure of Example 1, to obtain 20 g of the pure title compound (purity: 99%, yield: 91%).

EXAMPLE 27

Synthesis of bicyclo[3,2,2]non-8-ene-2-yl methylmalonic acid

To a solution containing sodium malonate (17 g) of Example 7 in dry tetrahydrofuran (100 g), bicyclo[3,2,2] non-8-ene-2-methyl chloride (17.1 g) obtained in Preparation Example 9 is slowly added, and the reaction is carried out at −20° C. in a nitrogen atmosphere for 1 hour, and then at 50° C. for 24 hours. Then, the reaction mixture is worked up as in the procedure of Example 1, to obtain 22 g of the pure title compound (purity: 99%, yield: 94%).

EXAMPLE 28

Synthesis of poly(5-norbornene-2-carboxyl-3-hydroxymethylethylbutylcarboxylate/maleic anhydride/norbornenee/5-norbornene-2-carbonyl di-tert-butylmalonate)

In tetrahydrofuran (25 ml), 5-norbornene-2-carboxylic-3-hydroxymethylethylbutylcarboxylate (12 mmol), maleic anhydride (100 mmol), norbornenee (30 mmol), 5-norbornene-2-carbonyl di-tert-butylmalonate (58 mmol) and AIBN (0.30 g) are dissolved, and the reaction is carried out at 65° C. for 10 hours. After the reaction is completed, the reaction mixture is poured into petroleum ether to produce a pure solid, which is filtered and dried to obtain the compound represented by Chemical Formula 6 (yield: 42%).

EXAMPLE 29

The copolymer (10 g) obtained in Example 28 and triphenylsulfonium triplate (0.12 g) as an inorganic photoacid generator are dissolved in ethyl 3-ethoxypropionate solvent (60 g), and the solution is filtered with a 0.10 μm filter to give a photoresist composition. The composition is spin-coated on a silicon wafer, which is then baked at 110° C. for 90 seconds. After baking, the wafer is exposed to light by using an ArF laser exposer device, and then baked again at 110° C. for 90 seconds. After the completion of baking, it is developed by a 2.38 wt % aqueous tetramethylammonium hydroxide solution for 40 seconds to obtain 0.12 μm of L/S pattern as illustrated in FIG. 1.

The carboxyl-containing alicyclic compound of the present invention represented by Chemical Formula 1, is useful as a monomer for synthesizing a photoresist resin for an ArF, E-beam, X-ray or EUV light source which can be applied to form a high-density micro-pattern of not more than 0.15 μm (DRAM of 1 G or more). The compound has a high purity and a low price, so that a photoresist resin of high performance can be economically produced on a large scale therefrom.

What is claimed is:

1. A photoresist polymer comprising at least one monomer represented by the following Chemical Formula 1:

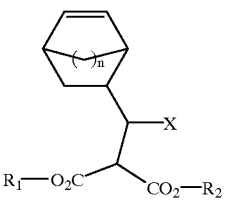

wherein, $R_1$ and $R_2$, which may be identical to or different from each other, represent hydrogen or a tert-butyl group; X represents hydrogen, hydroxy or oxygen; and n represents a number from 1 to 3.

2. A photoresist polymer according to claim 1, wherein said monomer is selected from a group consisting of 5-norbornene-2-carbonyl di-tert-butyl malonate; bicyclo[2,2,2]oct-5-ene-2-carbonyl di-tert -butyl malonate; bicyclo[3,2,2]non-8-ene-2-carbonyl di-tert-butyl malonate; 5-norbornene-2-carbonyl mono-tert-butyl malonate; bicyclo[2,2,2]oct-5-ene-2-carbonyl mono-tert-butyl malonate; bicyclo[3,2,2]non-8-ene-2-carbonyl mono-tert-butyl malonate; 5-norbornene-2-carbonyl malonic acid; bicyclo[2,2,2]oct-5-ene-2-carbonyl malonic acid; bicyclo[3,2,2]non-8-ene -2-carbonyl malonic acid; 5-norbornene-2-yl di-tert-butylhydroxymethyl malonate; bicyclo[2,2,2]oct-5-ene-2-yl di-tert-butylhydroxymethyl malonate; 5-norbornene-2-yl mono-tert-butylmethyl malonate; bicyclo[2,2,2]oct-5-ene-2-yl mono-tert-butylmethyl malonate; bicyclo[3,2,2]non-8-ene-2-yl mono-tert-butylmethyl malonate; 5-norbornene-2-yl hydroxymethylmalonic acid; bicyclo[2,2,2]oct-5-ene-2-yl hydroxymethylmalonic acid; bicyclo[3,2,2]non-8-ene-2-yl di-tert -butylmethyl malonate; 5-norbornene-2-yl mono-tert-butylmethyl malonate; bicyclo[2,2,2]oct-5-ene-2-yl mono-tert-butylmethyl malonate; bicyclo[3,2,2]non-8-ene-2-yl mono-tert-butylmethyl malonate; 5-norbornene-2-yl methylmalnonic acid; bicyclo[2,2,2]oct-5-ene-2-yl methylmalonic acid; and bicyclo[3,2,2]non-8-ene-2-yl methylmalonic acid.

* * * * *